United States Patent
Miwa et al.

(10) Patent No.: US 6,423,005 B1
(45) Date of Patent: Jul. 23, 2002

(54) ULTRASONIC DIAGNOSTIC APPARATUS

(75) Inventors: Yuichi Miwa, Chofu; Ryuichi Shinomura, Higashimatsuyama; Hirotaka Baba; Satoshi Tamano, both of Kashiwa, all of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/762,954

(22) PCT Filed: Aug. 17, 1999

(86) PCT No.: PCT/JP99/04419
§ 371 (c)(1), (2), (4) Date: Feb. 15, 2001

(87) PCT Pub. No.: WO00/10463
PCT Pub. Date: Mar. 2, 2000

(30) Foreign Application Priority Data

Aug. 18, 1998 (JP) .......................... 10-231231

(51) Int. Cl.$^7$ ................................. A61B 8/00
(52) U.S. Cl. ..................................... 600/443
(58) Field of Search ................ 600/437, 443, 600/447; 73/602

(56) References Cited

U.S. PATENT DOCUMENTS

| | | | | |
|---|---|---|---|---|
| 5,388,461 A | * | 2/1995 | Rigby | 600/442 |
| 5,423,318 A | * | 6/1995 | Li et al. | 600/447 |
| 6,059,730 A | * | 5/2000 | Miwa et al. | 600/443 |
| 6,131,458 A | * | 10/2000 | Longdon et al. | 73/627 |

FOREIGN PATENT DOCUMENTS

| | | |
|---|---|---|
| JP | 1-135333 | 5/1989 |
| JP | 4-158847 | 6/1992 |
| JP | 6-070928 | 3/1994 |
| JP | 6-105841 | 4/1994 |
| JP | 7-116162 | 5/1995 |
| JP | 8-308839 | 11/1996 |
| JP | 8-317923 | 12/1996 |
| JP | 9-103429 | 4/1997 |
| JP | 10-66694 | 3/1998 |

OTHER PUBLICATIONS

IEEE Transactions on Ultrasonic, Ferroelectrics, and Frequency Control, vol. 39, No. 6, Nov. 1992, pp. 700–707.
IEEE 1991 Ultrasonic Symposium Proceeding, pp. 1189–1193.

* cited by examiner

Primary Examiner—Francis J. Jaworski
(74) Attorney, Agent, or Firm—Mattingly, Stanger & Malur, P.C.

(57) ABSTRACT

An ultrasonic diagnostic apparatus in which the distortion of the received wave signal due to the ununiformity of the interior of an human body can be reduced accurately with a small circuit scale and an ultrasonic image of high resolution can be produced. The apparatus comprises a probe including an arrangement of elements for transmitting and receiving ultrasonic pulses to and from the interior of a subject, delay means for delaying the wave signal received from each element of the probe, and a plurality of adder means connected in series to the output of the delay means for adding the output signal of the preceding stages thereby to form an ultrasonic beam. The apparatus further comprises correlation means for calculating the correlation of two or more output signals of any of the adder means, and delay correcting means for estimating as many delay correction amounts as the input signals to the delay means from the time difference between adjacent signals generated from the correlation means thereby to correct the delay time of the received wave signal.

4 Claims, 6 Drawing Sheets

ULTRASONIC DIAGNOSTIC APPARATUS

TECHNICAL FIELD

The present invention relates to an ultrasonic diagnostic apparatus, or in particular to a technique effectively applicable to the correction of the delay time distribution of the received signals of a probe attributable to the fact that the interior of a subject is an ununiform medium.

BACKGROUND ART

In the conventional ultrasonic diagnostic apparatus, an ultrasonic wave is transmitted to a subject from an ultrasonic probe including an arrangement of a plurality of ultrasonic transducers (elements), the reflected wave thereof is received and given a delay time distribution as a received wave signal thereby to generate an ultrasonic beam having a directivity in a predetermined direction, thus producing a tomogram of the subject. The ultrasonic diagnostic apparatus, which is free of a radiation exposure unlike the other diagnostic apparatuses and can clearly plot the flesh easily without using a contrast medium as described above, is an indispensable diagnostic apparatus in wide fields of applications. As compared with the X-ray apparatus, however, the resolution of the ultrasonic diagnostic apparatus is still low and is expected to be improved further. In a technique for improving the resolution of the ultrasonic diagnostic apparatus, the amount of the phase shift caused by the ununiform medium in the subject is measured, and based on this phase shift amount, the delay time distribution applied to the received wave signals is corrected, and then the received wave signals corresponding to the respective ultrasonic transducers are added.

First, FIG. 9 shows a diagram for explaining the delay time distribution for forming an ultrasonic beam of high resolution in a human body constituting an ununiform medium. The correction of the pulse wave front in the ununiform medium will be explained with reference to FIG. 9. In the description that follows, only the operation at the time of receiving the ultrasonic wave will be explained for simplicity's sake.

In the case of a uniform medium with a known sound velocity, the wave front (the wave front of the received wave signal) of the pulse reflected from a reflector 906 reaches transducers 901 to 905 as an ideal wave front. In the process, due to the relative positions of the reflector 906 and the transducers 901 to 905, the reflected pulse reaches the transducer 903 earliest and the transducers 901, 905 latest. In order to assure the same arrival time of all the reflected pulses, the pulses received by the transducers 902 to 904 are given an appropriate delay. As a result, the same arrival time is secured for all the reflected pulses, and by the subsequent addition thereof, only the pulses received from the intended direction are amplified thereby to form a tomogram of a high resolution. In the case of a uniform medium of a known sound velocity, the delay to be given could be analytically determined as described below.

Assume that the distance between the transducers 901 to 905 and the reflector 906 is Li ($1 \leq i \leq 5$), the initial sound velocity of the ultrasonic diagnostic apparatus is c, the delay time given to the received wave signals of the transducers 901 to 905 is $\tau i$ ($1 \leq i \leq 5$), and the maximum value of Li ($1 \leq i \leq 5$) is Lmax. Then, $\tau i$ can be expressed by equation 1 below.

$$\tau i = (Lmax - Li)/c \qquad (1)$$

Actually, however, an ununiform medium 907 exists between the transducers 901 to 905 and the reflector 906, and therefore the pulse wave front assumes a distorted wave front 908. As a result, although $\tau i$ is optimum as an initial delay time given to the received wave signal of each transducer, the initial delay time is required to be corrected by an amount taking the distorted wave front 908 into consideration in order to produce a tomogram of a high resolution.

A technique for measuring this correction amount is described in "IEEE Transactions on Ultrasonic, Ferroelectrics and Frequency Control, Vol. 39, No. 6, pp. 700–707, 1992 (hereinafter referred to as "reference 1") or "IEEE 1991 Ultrasonics Symposium Proceeding pp. 1189–1193, 1991" (hereinafter referred to as "reference 2"). The technique described in these references is for correcting the effect that is had on the pulse wave front by an object having a different sound velocity, i.e. an ununiform medium which may exist between transducers for transmitting and receiving an ultrasonic wave and a reflector for reflecting the ultrasonic wave. According to this correcting technique, first, the amount of the phase shift of the reflected pulses resulting from the deviation of propagation time of the ultrasonic wave due to the ununiform medium is calculated by the correlating operation between all adjacent transducers. Then, based on the result of this calculation, the delay time of delay means is corrected thereby to correct the distortion of the pulse wave front due to the propagation of the ultrasonic wave through the ununiform medium for an improved resolution of the ultrasonic image.

The phase shift amount is determined using correlators for detecting adjacent phase shift of the outputs of the delay means for delaying the received wave signals of the transducers, for example. As a method of measuring the phase shift amount using the correlators, a technique is described in JP-A-1-135333 (hereinafter referred to as "reference 3"). According to the measuring technique described in reference 3, first, a delay time (initial delay time) is set as an initial value of delay means for giving a delay time distribution on the assumption that an human body is a uniform medium having a known sound velocity. Then, the delay process, i.e. the phasing of the received wave signals is carried out. After that, the phase shift amount between adjacent received wave signals after the delay process, i.e. the phase shift amount between the output signals of the delay means is calculated using correlators, and based on this arithmetic output, the phase shift amount for the initial delay time is corrected. In this way, the resolution of the ultrasonic wave is improved by correcting the phase shift caused by the ununiform medium in the human body.

DISCLOSURE OF THE INVENTION

As the result of studying the prior art described above, the present inventor has discovered the following problem points.

The conventional ultrasonic diagnostic apparatus poses the problem that as many correlators as the outputs of the delay means less 1, i.e. the number of the ultrasonic transducers less 1 are required for calculating the correlation between all the adjacent outputs of the delay means, resulting in a large circuit scale required for signal processing.

A technique for solving this problem is incorporated in an ultrasonic diagnostic apparatus described in JP-A-9-103429 (hereinafter referred to as "reference 4") filed by the same applicant. The ultrasonic diagnostic apparatus described in reference 4 comprises delay means for giving a different delay time distribution for each of the received wave signals output from ultrasonic transducers, first adding means for reducing the number of signals by adding the received wave signals output from the delay means, i.e. the received wave signals after phasing, second adding means for generating a single ultrasonic beam by adding the received wave signals output from the first adding means, and correlating means for performing the correlation calculation of adjacent output signals (adjacent received wave signals) from the received wave signals output from the first adding means and measuring the phase shift amount between the adjacent output signals. This ultrasonic diagnostic apparatus is so configured as to comprise Na delay means corresponding to Na ultrasonic transducers, for example, and the first adding means adds each two or more of the Na adjacent inputs to reduce the number of the outputs to Nb. In the ultrasonic diagnostic apparatus described in reference 4, therefore, correlating means can be configured with Nb-1 correlators corresponding to the first adding means so that the correction amount of the initial delay time, i.e. the phase shift amount can be measured with a small circuit scale.

With the ultrasonic diagnostic apparatus described in reference 4, the phase shift amount calculated in each correlator fails to coincide with the number of delay means, and therefore means is required to set a correction amount given to each delay means from the phase shift amount detected by the correlating means. Reference 4, however, includes no description of a method of calculating the correction amount given to each delay means nor a configuration for obviating the inconvenience, and therefore poses the problem that the phase shift amount detected by each correlator cannot be reflected in each delay means.

An object of the present invention is to provide a technique for making it possible to reduce the distortion of the received wave signal due to the ununiformity in an human body accurately with a small circuit scale.

Another object of the invention is to provide a technique for making it possible to improve the resolution of an ultrasonic image.

Still another object of the invention is to provide a technique for making it possible to improve the efficiency of diagnosis of a subject.

The above and other objects and the novel features of the invention will be made apparent by the description of the present specification and the accompanying drawings.

Representative features of the invention disclosed by this application will be briefly explained below.

(1) An ultrasonic diagnostic apparatus comprises a probe including an arrangement of elements for transmitting and receiving ultrasonic pulses to and from the interior of a subject, delay means for delaying the received wave signal from each element of the probe, and a plurality of adding means connected in series to the output of the delay means for adding the output signal of the preceding stage thereby to form an ultrasonic beam, the apparatus further comprising correlating means for performing the correlation calculation of two or more output signals of any of the adding means and delay correcting means for estimating as many delay correction amounts as the input signals to the delay means from the time difference between adjacent signals generated from the correlating means and correcting the delay time of the received wave signals.

(2) The ultrasonic diagnostic apparatus as described in (1) above, wherein said delay correcting means includes linear arithmetic means.

(3) The ultrasonic diagnostic apparatus as described in (1) or (2) above, wherein the number of the input signals to the delay means is a multiple equal to the power of 2 of the input signals to the correlating means.

(4) The ultrasonic diagnostic apparatus as described in any one of (1) to (3) above, wherein the delay correcting means estimates the delay correction amount of the elements other than one of the outermost elements with reference to the delay time for said one of the outermost elements.

According to the means of (1) to (4) described above, the correlating means calculates the time difference between adjacent signals by the correlating operation of two or more output signals of the adding means, and based on this time difference, the delay correcting means estimates as many delay correction amounts as the input signals to the delay means, and the delay means corrects the delay time of the received wave signals based on the delay correction amounts. In this way, the number of the time differences calculated by the correlating means, i.e. the number of the adjacent signals input to the correlating means can be reduced, and therefore the circuit scale of the correlating means can be reduced. In the process, by estimating the delay correction amount for each ultrasonic transducer from the time difference between the adjacent signals by the delay correcting means after addition, the sound velocity information loss by the addition for each ultrasonic transducer can be restored. Therefore, the distortion of the received wave signals, i.e. the phase shift of the received wave signals caused by the ununiformity in the subject can be eliminated accurately with a small circuit scale. As a result, the distortion of the ultrasonic beam output from the adding means can be reduced, thereby making it possible to improve the resolution of the ultrasonic image. Consequently, the S/N of the ultrasonic image can be improved. Thus, the diagnosis efficiency can be improved.

At the same time, the circuit configuration can be simplified by configuring the delay correcting means with a linear arithmetic operation, and therefore a fast arithmetic operation is made possible. Also, the circuit scale of the delay correcting means can be reduced, and therefore the ultrasonic diagnostic apparatus can be reduced in size.

BEST MODE FOR CARRYING OUT THE INVENTION

First Embodiment

Figure 1:
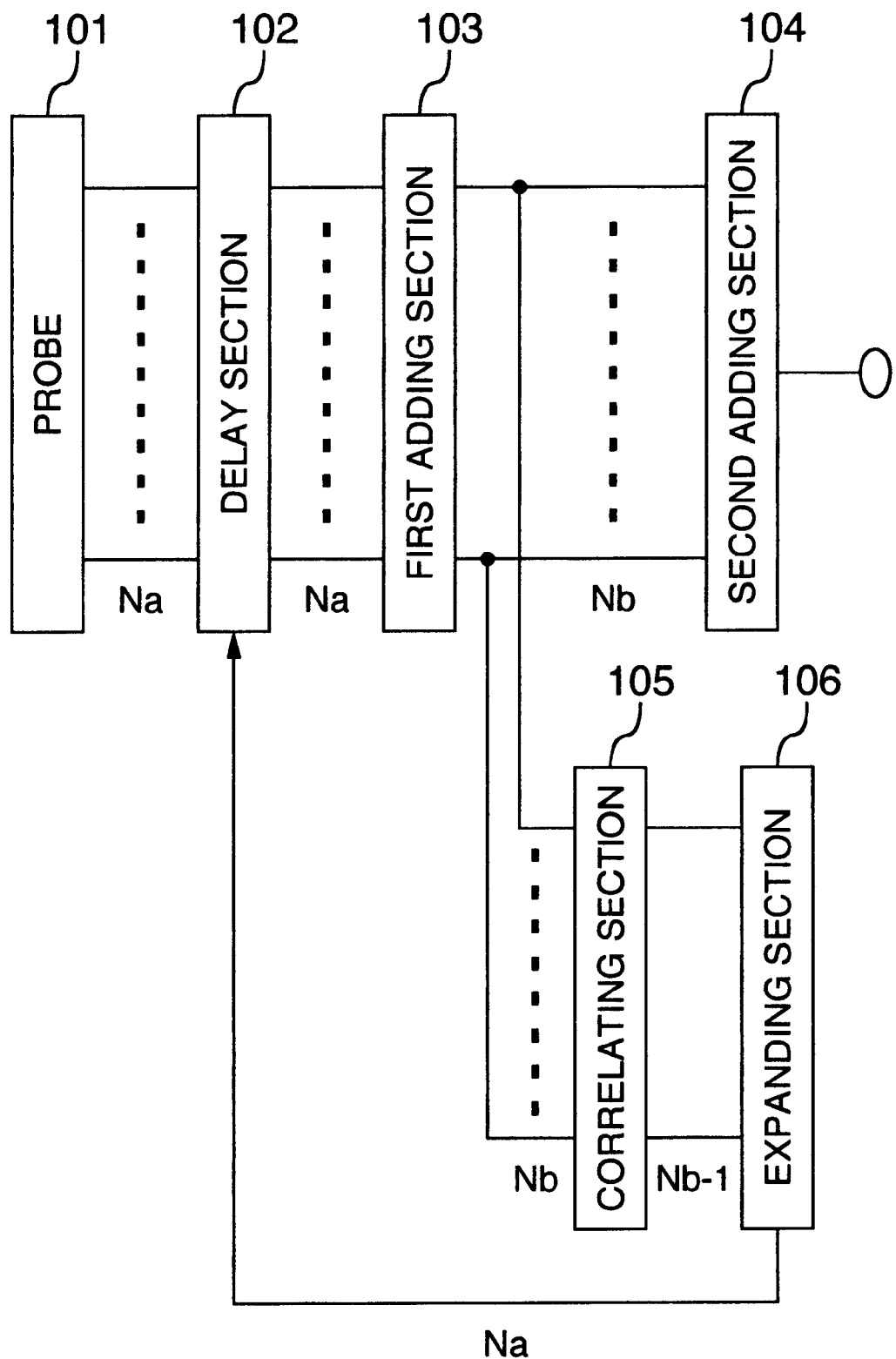
FIG. 1 is a block diagram showing a general configuration of an ultrasonic diagnostic apparatus according to a first embodiment of the present invention.

FIG. 1 is a block diagram for explaining a general configuration of an ultrasonic diagnostic apparatus according to a first embodiment of the invention. Reference numeral 101 designates a probe, numeral 102 a delay section, numeral 103 a first adding section, numeral 104 a second adding section, numeral 105 a correlating section, and numeral 106 an expanding section. In the ultrasonic diagnostic apparatus according to this embodiment shown in FIG. 1, the configuration of only the essential parts is shown for facilitating the explanation, and other well-known component elements including the amplifier section, the detector section and the display section are not shown. Also, the operation during the ultrasonic wave transmission is similar to that for the conventional diagnostic apparatus and therefore only the operation during the ultrasonic wave receiving will be explained. Further, according to the first embodiment, the first adding section 103 and the second adding section 104 compose the adding means.

In FIG. 1, the probe 101 has Na ultrasonic transducers (arrangement of elements) each of which is connected to the delay section 102. The number Na of the ultrasonic transducers is generally 64 or 128, but the present invention is of course also applicable to other numbers of the ultrasonic transducers.

The delay section 102 is a means, which after converting the received wave signals constituting analog signals input from the ultrasonic transducers of the probe 101 into digital signals (received wave digital signals), performs the delay process based on an initial delay time or a corrected delay time output from the expanding section 106 (hereinafter referred to as "the corrected delay time"). The received wave digital signals after the delay process are sent to the first adding section 103.

The first adding section 103 is a well-known adding means for sequentially adding the received wave digital signals after the delay process input from the delay section 102. According to this embodiment, the first adding section 103 includes Nb (=Na/2) adders for adding, for example, each two adjacent received wave digital signals of odd and even numbers in the Na outputs of the delay section 102. Thus, the number of inputs to the first adding section 103 is Na, and the number of outputs thereof is Nb=Na/2. The first adding section 102 will be described in detail later.

The second adding section 104 is a well-known adding means for forming an ultrasonic beam by adding the received wave digital signals from the first adding section 103 into a single signal. The correlating section 105 is a well-known correlating means for calculating the inter-signal phase shift amount by the correlating operation between adjacent signals of the Nb received wave digital signals generated from the first adding section 103 and includes Nb-1 correlators for calculating the phase shift amount between adjacent received wave digital signals. The result of this arithmetic operation is sent to the expanding section 106. The correlating section 105 has Nb input terminals and Nb-1 output terminals. By the way, a method of calculating the phase shift amount in the correlator is disclosed in detail, for example, in JP-A-1-135333 constituting reference 3, and therefore will not be explained in detail.

The expanding section 106 is means for calculating the delay time corresponding to each of the Na ultrasonic transducers based on the Nb-1 phase shift amounts calculated by the correlating section 105 and setting the said delay time in the delay section 102. The expanding section 106 can be configured with an interpolating operation means and an extrapolating operation means well known in the information processing system. A detailed description will be given later.

Figure 2:
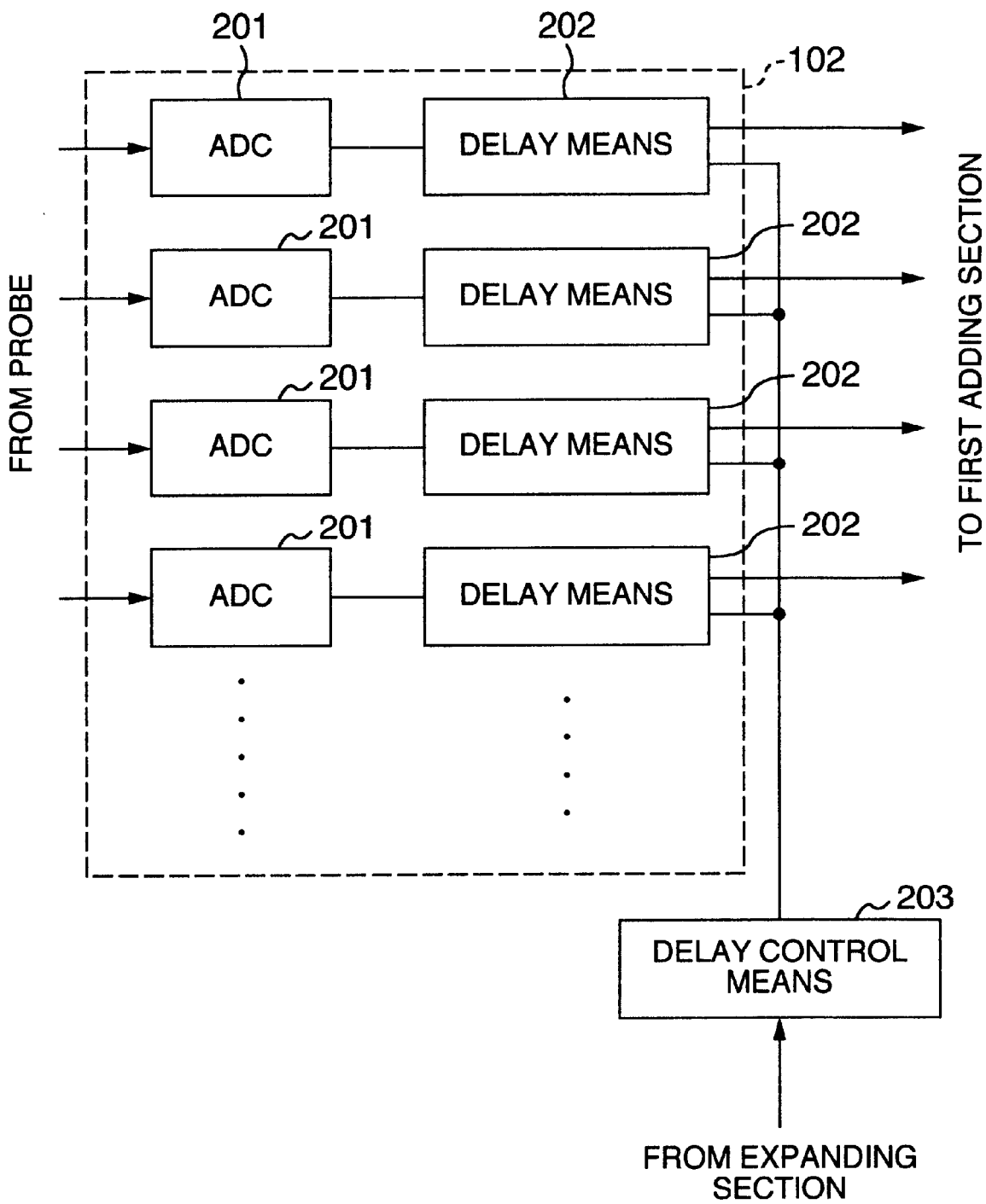
FIG. 2 is a block diagram showing a configuration of a delay section according to the aforementioned first embodiment.

FIG. 2 is a block diagram for explaining a general configuration of the delay section according to the first embodiment, in which numeral 201 designates ADCs and numeral 202 delay means.

As shown in FIG. 2, the delay section according to this embodiment includes ADCs 201 and delay means 202 in one-to-one correspondence with each of the Na ultrasonic transducers.

The ADC 201 is a well-known A/D converter for converting the received wave signal constituting an analog electrical signal corresponding to the reflected wave received by each ultrasonic transducer making up the probe 101 into a received wave digital signal.

The delay means 202 is a well-known digital delay means including a SRAM or the like, for example, in which the read address of the received wave digital signal stored in the SRAM is controlled by delay control means 203 thereby to delay the signal for a predetermined time.

The delay control means 203 is a means for setting a read address of the received wave digital signal in each delay means immediately after starting the ultrasonic measurement, based on the initial delay time stored in the storage means such as a magnetic disk unit not shown in the delay process. For the subsequent delay process, for example, the time obtained by adding the correction amount generated from the expanding section 106 to the initial delay time is used as a delay time, and based on this delay time, a read address of the received wave digital signal is set in each delay means. The initial delay time according to this embodiment, however, is the delay time based on the assumption that an human body is a uniform medium having a known sound velocity.

Now, the operation during the wave receiving process of the ultrasonic diagnostic apparatus according to this embodiment will be explained with reference to FIGS. 1 and 2. First, the wave receiving operation immediately after starting the measurement will be explained, followed by the explanation of the subsequent wave receiving operation.

The reflected wave received by the probe 101 is converted into a received wave signal by each ultrasonic transducer and sent to the delay section 102, and after each ADC 201 corresponding to each ultrasonic transducer converts the received wave signal into a received wave digital signal, the received wave digital signal is sent to the delay means 202 connected to each ADC 201. The received wave digital signals are sequentially written in the delay means 202.

The received wave digital signals written in the SRAMs of the delay means 202 are started to be read from all the delay means 202 in response to the read instruction of the delay control means 203 upon the lapse of a predetermined time, and sent to the first adding section 103. The read start address, however, is an address value determined by the delay control means 203 based on the initial delay time read from storage means not shown. Also, according to this embodiment, the read address is calculated based on the ultrasonic transducer nearest to the center of the transmitted wave.

The received wave digital signals read from the delay means 202 are added by the first adding section 103 into Nb received wave digital signals by sequentially adding two odd and even outputs out of the Na outputs of the delay section 102, and further added into a single signal by the second adding section 104 thereby to form an ultrasonic beam. At the same time, the correlating section 105 calculates the phase shift amount between adjacent received wave data signals among the Nb received wave digital signals output from the first adding section 103.

The expanding section 106 calculates Na correction amounts corresponding to the ultrasonic transducers based on the aforementioned phase shift amount as a delay time for the next received wave signal and outputs them to the delay section 102, which reads the data by correcting the read address of the next received wave digital signal based on these correction amounts.

In this way, with the ultrasonic diagnostic apparatus according to this embodiment, based on the phase shift amount between the adjacent received wave digital signals calculated from the output of the first adding section 103, the expanding section 106 calculates the correction amount for each ultrasonic transducer, and based on this correction amount, the delay control means 203 sequentially changes the address for reading the received wave digital signals from the delay means. Thus, the number of correlators can be reduced, which results to a reduced circuit scale. Also, according to this invention, the phase shift amount of the received wave digital signal thus added is calculated by the correlating section 105. Therefore, even in the case when the response or the signal input from a specific transducer is lost by a disconnection of the signal line or the like, the phase shift amount can be determined without reducing the calculation accuracy. As a result, the reduction in correction accuracy of the expanding section 106 can be prevented, thereby making it possible to prevent the deterioration of the image quality of the ultrasonic image.

<<Expanding operation>>

Figure 3:
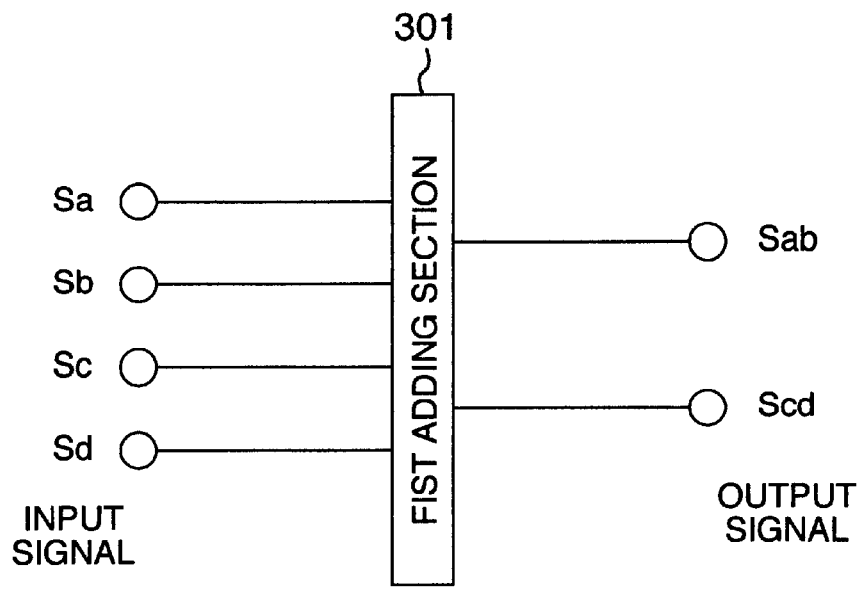
FIG. 3 is a block diagram showing a configuration of an adding section according to the aforementioned first embodiment.
Figure 4:
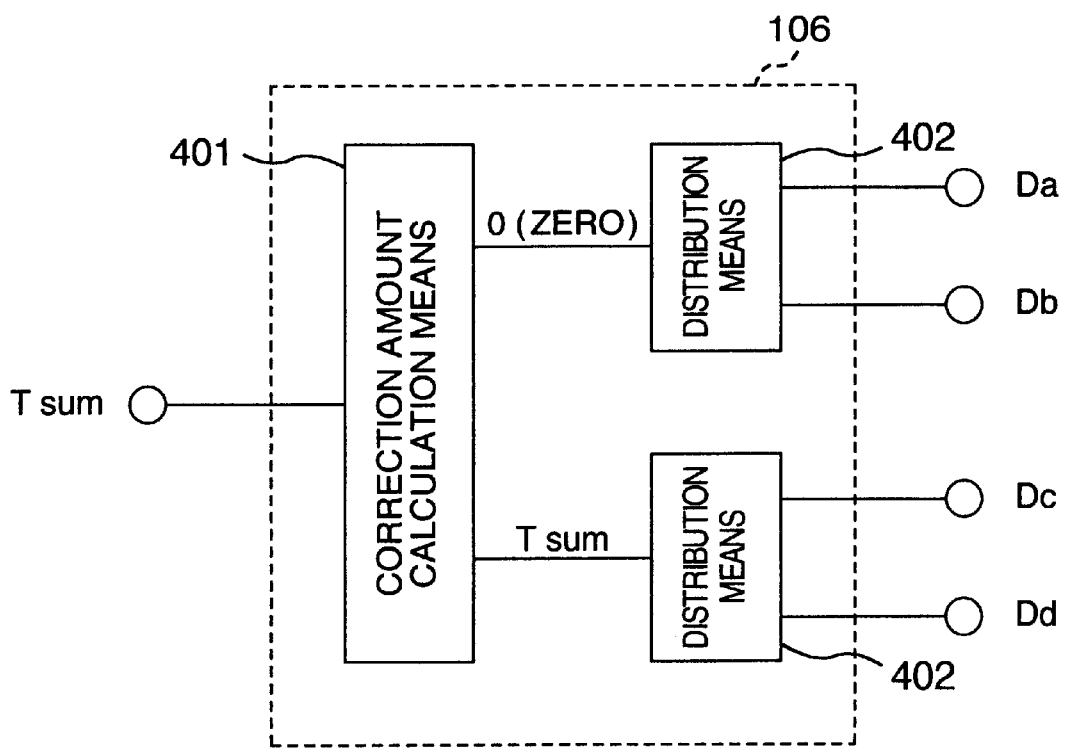
FIG. 4 is a block diagram showing a configuration of an expanding section according to the aforementioned first embodiment.

FIG. 3 is a block diagram for explaining a general configuration of the first adding section according to this embodiment, and FIG. 4 is a diagram for explaining a general configuration of the expanding section according to the first embodiment. The correcting operation of the expanding section according to this embodiment will be explained with reference to FIGS. 3 and 4. The description that follows deals with the case where the probe 101 has four ultrasonic transducers, to which the invention is not limited.

In FIGS. 3 and 4, Sa designates a received wave digital signal after the delay process from the first ultrasonic transducer, Sb a received wave digital signal after the delay process from the second ultrasonic transducer, Sc a received wave digital signal after the delay process from the third ultrasonic transducer, Sd a received wave digital signal after the delay process from the fourth ultrasonic transducer, Sab a first sum signal obtained by adding the first received wave digital signal Sa and the second received wave digital signal Sb, Scd a second sum signal obtained by adding the third received wave digital signal Sc and the fourth received wave digital signal Sd, Da the correction amount corresponding to the first ultrasonic transducer, Db the correction amount corresponding to the second ultrasonic transducer, Dc the correction amount corresponding to the third ultrasonic transducer, Dd the correction amount corresponding to the fourth ultrasonic transducer, 401 a correction amount calculating means, and 402 a distributing means.

First, prior to explaining the expanding operation of the expanding section according to this embodiment, an explanation will be given of the case in which the phase shift amount between adjacent signals is calculated based on the output of the delay section 102 and the delay time is corrected based on the result of calculation.

In the case where the signals are not added by the first adding section 103, i.e. in the case where the phase shift amount is detected by the correlating section 105 based on the output of the delay section 102, the correlating section 105 carries out the calculation of the adjacent correlation between the first received wave digital signal Sa and the second received wave digital signal Sb, the calculation of the adjacent correlation between the second received wave digital signal Sb and the third received wave digital signal Sc, and the calculation of the adjacent correlation between the third received wave digital signal Sc and the fourth received wave digital signal Sd in FIG. 3. This determines the time difference (phase shift amount) Tab between the first received wave digital signal Sa and the second received wave digital signal Sb, the time difference Tbc between the second received wave digital signal Sb and the third received wave digital signal Sc. and the time difference Tcd between the third received wave digital signal Sc and the fourth received wave digital signal Sd. The time differences Tab, Tbc, Tcd are each the time difference between adjacent signals, and therefore when used as a delay correction amount, are required to be converted into a time difference with a specified signal as a reference. According to the prior art, using the first received wave digital signal Sa as a reference, the correction amount of 0 (zero) is determined for the first received wave digital signal Sa, the correction amount of Tab is determined for the second received wave digital signal Sb, the correction amount of Tab+Tbc is determined for the third received wave digital signal Sc, and the correction amount of Tab+Tbc+Tcd is determined for the fourth received wave digital signal Sd. In the process, the first to fourth received wave digital signals Sa, Sb, Sc, Sd correspond in one-to-one relation to the input signals of the delay section 102, and therefore all the four input signals of the delay section 102 can be corrected independently.

In the case where the signals are added by the adding section 103, i.e. in the ultrasonic diagnostic apparatus according to the first embodiment of the invention, the correlating section 105 carries out the calculation of the adjacent correlation between the first sum signal Sab and the second sum signal Scd generated from the first adding section 301. Assuming that the phase shift-amount is Tsum, i.e. the time difference obtained in the process, this time difference Tsum is calculated between adjacent signals, and therefore when used as a delay correction amount, is required to be converted to a time difference with a specified signal as a reference. According to this embodiment, using the first sum signal Sab as a reference, the correction amount calculating means 401 sets the correction amount of the first sum signal Sab to 0 (zero), and the correction amount of the second sum signal Scd to Tsum. In view of the fact that the first and second sum signals Sab, Scd are not in one-to-one correspondence with the input signals to the delay section 102, however, the delay correction amounts 0 and Tsum determined by the correlation calculation are required to be expanded (converted) to the correction amounts of the first to fourth received wave digital signals Sa, Sb, Sc, Sd, respectively.

Now, the expansion of the correction amount in the ultrasonic diagnostic apparatus according to this embodiment will be explained with reference to FIG. 4.

In FIG. 4, distribution means 402 each include a well-known distributor for distributing and outputting the received wave digital signal Sab in two parts with the same value, for example.

With the ultrasonic diagnostic apparatus according to this embodiment, therefore, the distribution means 402 convert the correction amount 0 of the first sum signal Sab into correction amounts Da and Db corresponding to the first and second ultrasonic transducers, respectively, and the correction amount Tsum of the second sum signal Scd into correction amounts Dc and Dd corresponding to the third and fourth ultrasonic transducers, respectively, and outputs them to the delay control means 203 of the delay section 102. Specifically, in the expanding section 106 according to this embodiment, with the first sum signal Sab as a reference, the correction amount calculation means 401 determines 0 (zero) as the correction amount of the first sum signal Sab (first correction amount) and Tsum as the correction amount of the second sum signal Scd (second correction amount). Then, the distribution means 402 determines the correction amount 0 (zero) as the correction amounts corresponding to the first and second ultrasonic transducers associated with the first sum signal Sab, and the correction amount Tsum as the correction amounts corresponding to the third and fourth ultrasonic transducers associated with the second sum signal Scd, thereby setting the delay time for the next received wave signal in each ultrasonic transducer.

With this relation between the delay time after correction and the input terminal of the delay section, even in the case where adjacent ultrasonic transducers are given two identical correction amounts, different initial delay time lead to different values of the delay time after correction, so that the accuracy of the ultrasonic beam output from the second adding section 104 can be improved. Thus, the image distortion of the ultrasonic image can be corrected accurately for an improved resolution. At the same time, the S/N of the ultrasonic image is improved with the improvement in the image distortion.

In the foregoing description, the number of signals after summing is 2, and therefore the time difference Tsum between adjacent signals directly constitutes an object of expanding operation. Nevertheless, the object of the expanding operation is not the time difference between adjacent signals determined by the correlation operation, but always is the time difference based on a specific signal. In the case where the number of signals after summing is 4 and three time differences T1, T2, T3 are detected in the correlation operation for the signals after summing, for example, the object of expanding operation is not (0, T1, T2, T3), but the time difference (0, T1, T1+T2, T1+T2+T3) based on a specific signal. This is also the case with the second and third embodiments described below.

As explained above, with the ultrasonic diagnostic apparatus according to the first embodiment, the correlating section 105 calculates the time difference between adjacent sum signals by the correlation operation of the Nb output signals of the first adding section 103, and based on the time difference, the correction amount calculation means 401 of the expanding section 106 calculates the correction amount between adjacent sum signals. Then, the distribution means 402 of the expanding section 106 distributes the correction amount between the sum signals to the correction amount for each ultrasonic transducer, and according to this correction amount, the delay control means 203 of the delay means 102 sets the delay time for the wave signal to be next received. In this way, the number of output signals from the correlation means 105, i.e. the number of correlators can be reduced to Nb-1. Thus, the circuit scale of the correlation means 105 can be reduced. At the same time, the expanding section 106 estimates the correction amount for each ultrasonic transducer from the time difference between the sum signals after addition. In this way, the sound velocity information for each ultrasonic transducer which has been lost by the addition of the received wave signals can be restored, and therefore the distortion of the received wave signal attributable to the ununiformity in an human body, i.e. the phase shift of the received wave signals can be removed accurately with a small circuit scale. Thus, the distortion of the ultrasonic beam output from the second adding section 104 can be reduced for an improved resolution of the ultrasonic image. As a result, the S/N of the ultrasonic image can be improved.

In the process, in view of the fact that the first embodiment is configured only to distribute the correction amount obtained from each sum signal to the ultrasonic transducer corresponding to the sum signal, the configuration of the expanding section 106 can be simplified and therefore the fast arithmetic operation is made possible. Also, since the circuit scale of the expanding section 106 can be reduced, a compact ultrasonic diagnostic apparatus can be obtained.

According to this invention, however, the hardware configuration makes it desirable that the value Na/Nb is the power of 2. This is in order to facilitate the circuit design by putting the number of input/output signals into order by the power of 2 in the case where the ultrasonic diagnostic apparatus shown in FIG. 1 is implemented by the digital signal processing. Further, from the viewpoint of both the correction accuracy and the circuit size, Na/Nb is optimally 2. By the way, the first adding section 103 can of course be configured with a plurality of adding sections connected in series. Similarly, the second adding section 104 can of course be configured with a plurality of adding sections connected in series.

Second Embodiment

Figure 5:
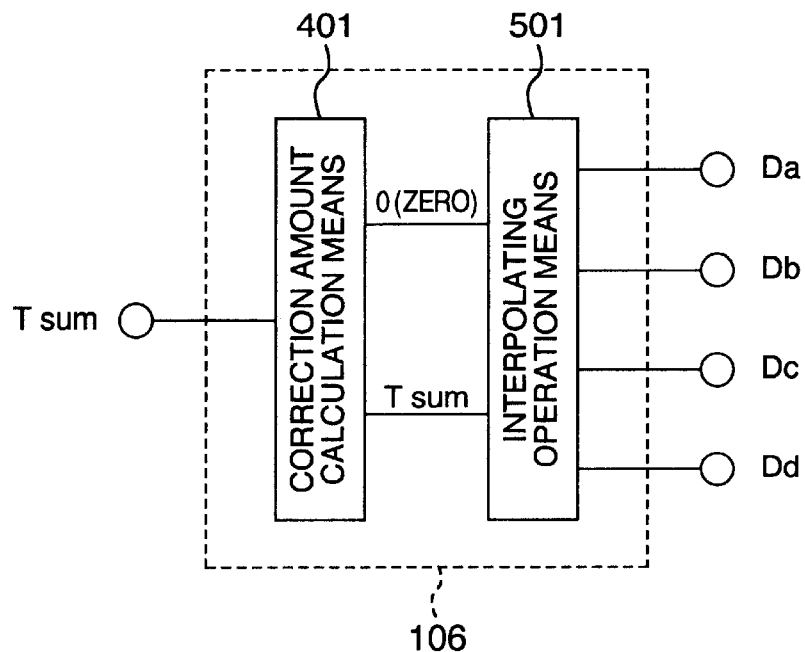
FIG. 5 is a block diagram showing a general configuration of the expanding section of an ultrasonic diagnostic apparatus according to a second embodiment of the invention.

FIG. 5 is a diagram for explaining a general configuration of the expanding section of an ultrasonic diagnostic apparatus according to a second embodiment of the present invention. Numeral 501 designates interpolating operation means. In the ultrasonic diagnostic apparatus according to this embodiment, only the configuration of the expanding section 106 is different, and the configuration of the other component parts is similar to that of the ultrasonic diagnostic apparatus according to the first embodiment. In this embodiment, therefore, only the expanding section 106 which has a different configuration will be explained in detail. The description that follows refers to the case where the number of the ultrasonic transducers of the probe 101 is 4, but the embodiment is of course applicable to the case where the probe 101 has more than 4 transducers.

In FIG. 5, interpolation means 501 is a well-known linear interpolation means, for example, for calculating the correction amounts Da, Db, Dc, Dd corresponding to the first to fourth ultrasonic transducers, respectively, by linear interpolation from a first correction amount corresponding to the first phase shift amount and a second correction amount corresponding to the second phase shift amount generated from the correction amount calculation means 401.

An explanation will be given of the case in which like in the first embodiment described above, for example, the correlating section 105 carries out the adjacent correlation operation for the first received wave digital signal Sab and the second received wave digital signal Scd thereby to determine the time difference between the first received wave digital signal Sab and the second received wave digital signal Scd.

In this case, like in the first embodiment described above, the time difference Tsum is the one between adjacent signals, and therefore the use of it as a delay correction amount requires the conversion into a time difference based on a specific signal. According to this embodiment, the correction amount calculation means 401 sets the correction amount of the first received wave digital signal Sab to 0 (zero) and the correction amount of the second received wave digital signal Scd to Tsum based on the first received wave digital signal Sab.

Then, the interpolation calculation means 501 according to the second embodiment sets the correction amount 0 (zero) of the first received wave digital signal Sab as a correction amount Da corresponding to the first ultrasonic transducer, sets the correction amount Tsum of the second received wave digital signal Scd as a correction amount Dc corresponding to the third ultrasonic transducer, and calculates the correction amounts Db, Dd corresponding to the second and fourth ultrasonic transducers by the linear interpolation operation based on these correction amounts. In this case, Tsum/2 is calculated as a value corresponding to the correction amount Db and 3Tsum/2 as a value corresponding to the correction amount Dd. And the interpolation operation means 501 outputs 0 (zero), Tsum/2, Tsum and 3Tsum/2 as the first to fourth correction amounts Da, Db, Dc and Dd corresponding to the first to fourth ultrasonic transducers, respectively. In the process, different delay time are set in the delay section 102 according to this embodiment, and therefore the grating lobe strength can be reduced. As a result, the resolution of the ultrasonic image can be improved more than in the ultrasonic diagnostic apparatus according to the first embodiment described above.

Figure 6:
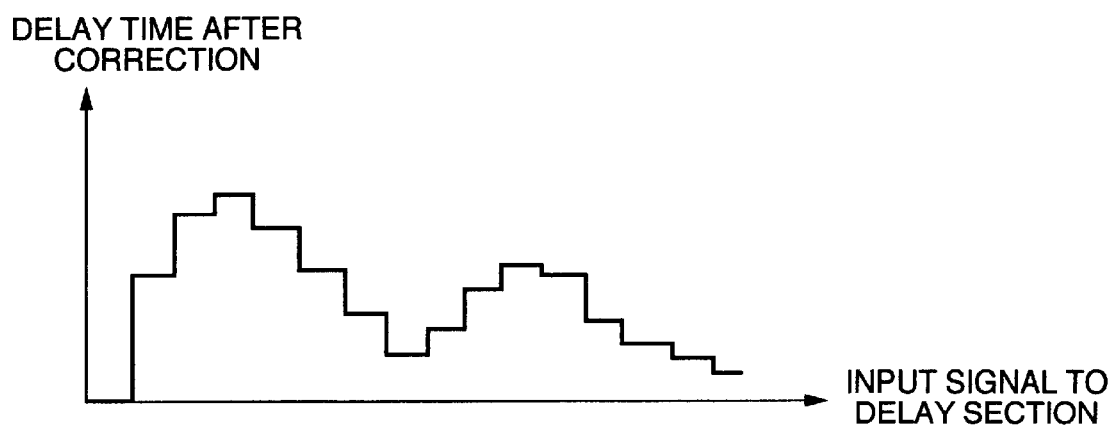
FIG. 6 is a diagram for explaining the relation between each received wave signal and the delay time after correction.

By the way, in the ultrasonic diagnostic apparatus according to this embodiment, the linear interpolation operation is performed as an interpolation operation in the interpolation operation means 501, to which the embodiment is not limited. For example, the parabolic interpolation, the spline interpolation, the Newton interpolation, the Bessel interpolation and other interpolation methods can of course be employed as an alternative. Also, as shown in FIG. 6, assume that each received wave signal applied to the delay section 102 is plotted along the abscissa and the delay time after correction is plotted along the ordinate. In the case where the same correction amount is used for the signals summed, the delay time after correction given to each signal by the delay section 102 are presented in steps, and the interval between the steps is equal to the width of each one of the summed signals associated with the corresponding ultrasonic transducer. Let the wavelength of the ultrasonic wave be $\lambda$, the interval of the steps be d and the angle at which the grating lobe appears from the direction of the main beam be $\theta$. The relation $\sin\theta = \lambda/d$ holds. In other words, the larger the number of the summed signals and the larger the interval d of the steps, the nearer to the main beam the grating lobe appears. As a result, although the method in which the same correction amounts are arranged for expansion has a high calculation speed, care must be exercised about the position of appearance of the grating lobe and the strength thereof.

Third Embodiment

Figure 7:
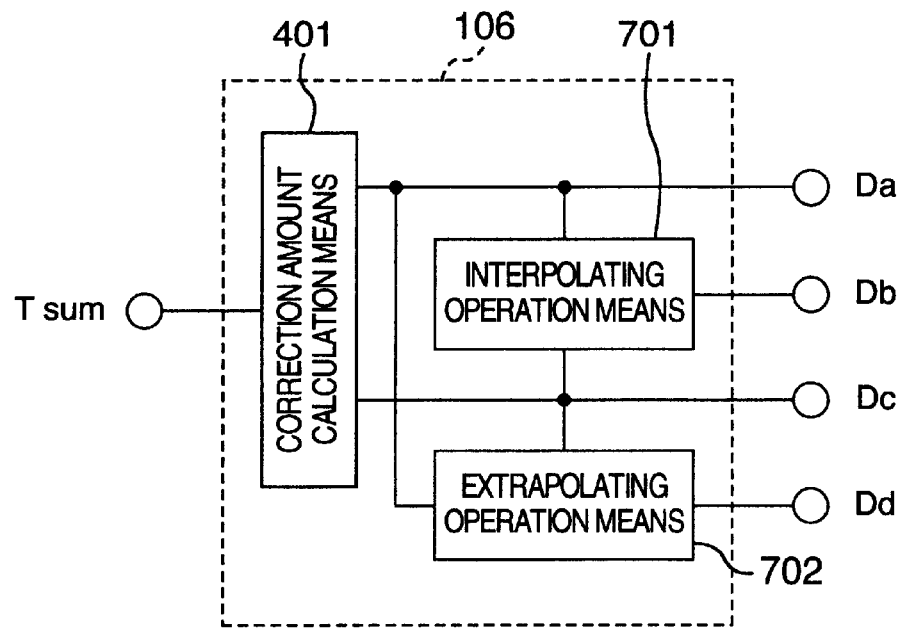
FIG. 7 is a block diagram showing a general configuration of the expanding section of an ultrasonic diagnostic apparatus according to a third embodiment of the invention.

FIG. 7 is a diagram for explaining a general configuration of an expanding section of an ultrasonic diagnostic apparatus according to a third embodiment of the present invention. Numeral 701 designates interpolating operation means and numeral 702 extrapolating operation means. The ultrasonic diagnostic apparatus according to the third embodiment is similar to the ultrasonic diagnostic apparatus according to the first embodiment with the exception of the configuration of the expanding section 106. In the present embodiment, therefore, only the expanding section 106 having a different configuration will be explained in detail. By the way, the description that follows refers to the case where the number of the ultrasonic transducers of the probe 101 is 4, to which the invention is not limited.

As shown in FIG. 7, in the expanding section of the ultrasonic diagnostic apparatus according to this third embodiment, the correction amount calculation means 401 calculates the correction amount Da with the first sum signal as a reference based on the time difference Tsum. In the process, the correction amount corresponding to an odd ultrasonic transducer, i.e. the first correction amount Da corresponding to the first ultrasonic transducer constituting a reference is 0, and the third correction amount Dc corresponding to the third ultrasonic transducer is Tsum.

The correction amount Db corresponding to an even ultrasonic transducer, i.e. the second ultrasonic transducer, on the other hand, is the average between the first correction amount Da and the third correction amount Dc adjacent to each other, i.e. Tsum/2, as calculated by the interpolation operation means 701 constituted of a well-known interpolation processor. Also, the fourth correction amount Dd corresponding to the fourth ultrasonic transducer is determined as 3Tsum/2 as calculated by the extrapolation calculation means 702 constituted of a well-known extrapolation processor from the adjacent third correction amount Dc and the next nearest odd correction amount, i.e. the first correction amount Da.

In this way, also according to the third embodiment, a different-value can be set for each ultrasonic transducer of the probe 101. Like in the second embodiment described above, therefore, the grating lobe strength can be reduced. At the same time, the initial delay time correction amounts of all the received wave signals can be calculated from the phase shift amount determined by the correlation calculation for the summed signals. As a result, the effect of ununiformity in an human body can be removed with high accuracy with a small circuit scale. Consequently the resolution of the ultrasonic image can be improved.

In this third embodiment, the interpolation operation means 701 is so configured as to determine the average value of adjacent two data as a correction amount therebetween, to which the invention is not limited. Instead, a well-known weighted mean or the like can of course be employed.

Fourth Embodiment

Figure 8:
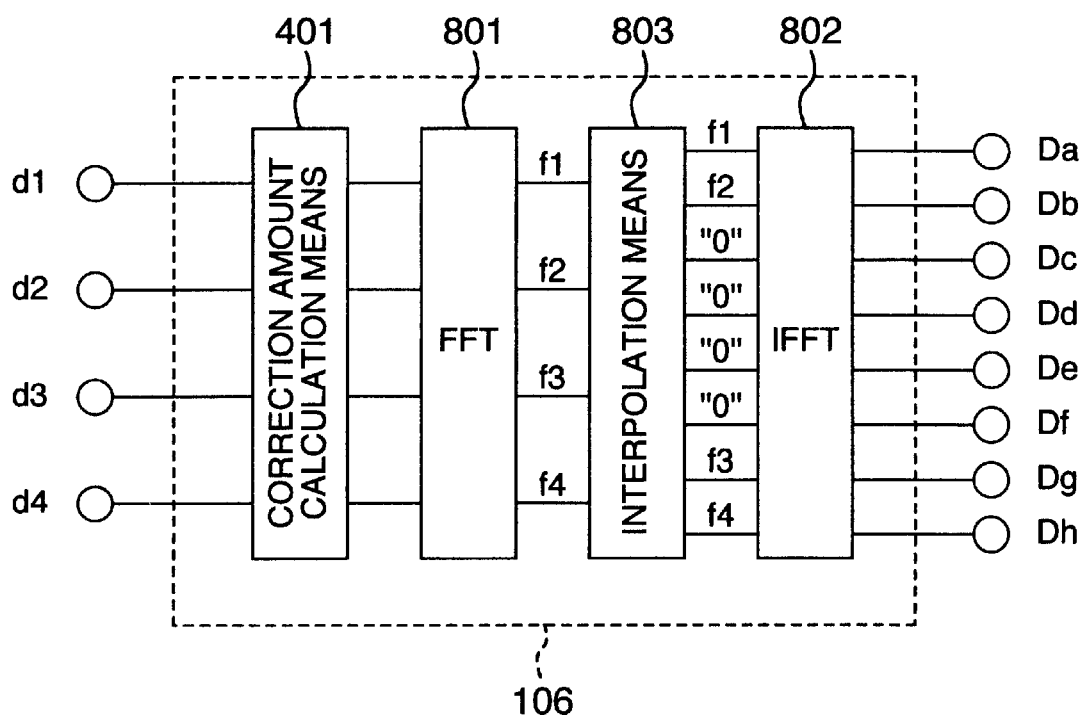
FIG. 8 is a block diagram showing a general configuration of the expanding section of an ultrasonic diagnostic apparatus according to a fourth embodiment of the invention.
Figure 9:
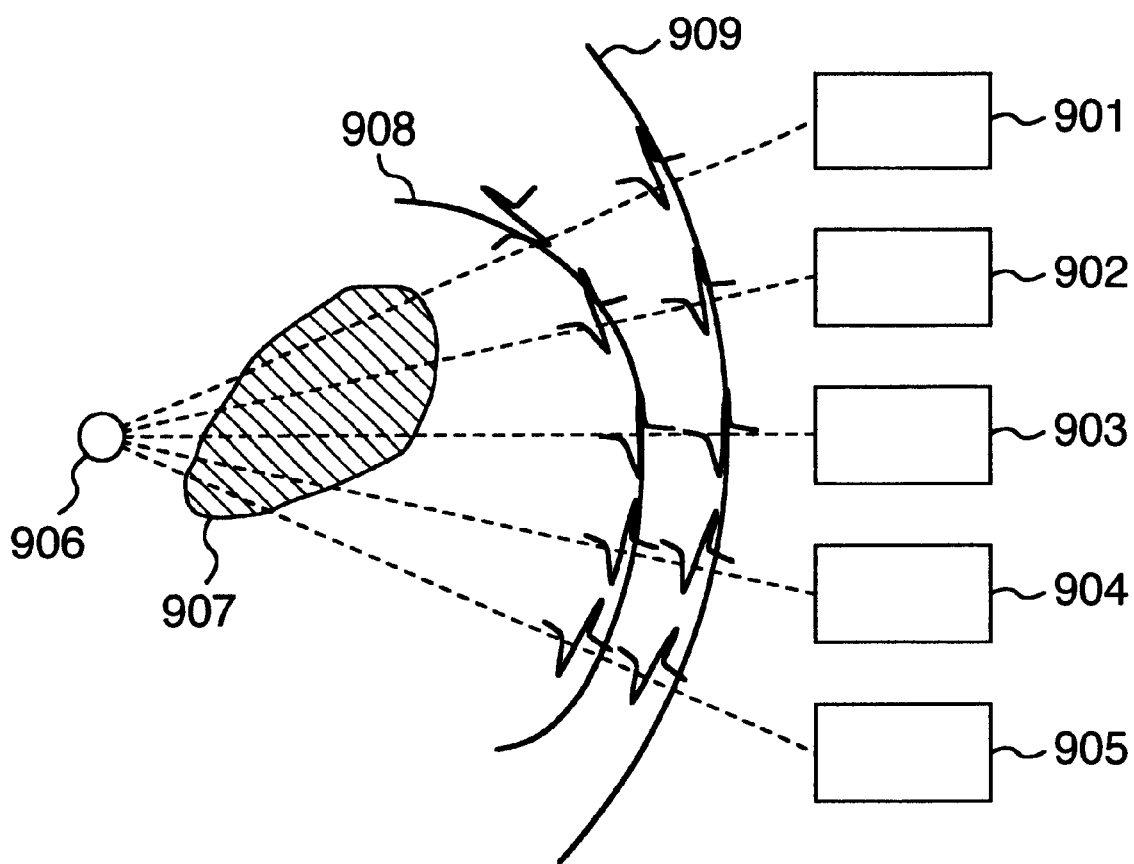
FIG. 9 is a diagram for explaining the delay time distribution for forming an ultrasonic beam of high resolution in a human body constituting an ununiform medium.

FIG. 8 is a diagram for explaining a general configuration of the expanding section of an ultrasonic diagnostic apparatus according to a fourth embodiment of the present invention. Numeral 801 designates FFT means and numeral 802 IFFT means. The ultrasonic diagnostic apparatus according to the fourth embodiment is similar to the ultrasonic diagnostic apparatus according to the first embodiment with the exception of the configuration of the expanding section 106. In the present embodiment, therefore, only the expanding section 106 having a different configuration will be explained in detail. By the way, the description that follows refers to the case where the number of the ultrasonic transducers of the probe 101 is 8, i.e. the output of the first adding section 103 is 4. The invention is of course applicable, however, also to the case where the number of the ultrasonic transducers is more than 4.

In FIG. 8, the FFT means 801 is a well-known 4-input 4-output FFT calculator (fast Fourier transformer), and the IFFT means 802 a well-known 8-input 8-output IFFT calculator (inverse fast Fourier transformer).

Now, an explanation will be given to the operation of the expanding section 106 of the ultrasonic diagnostic apparatus according to this embodiment, i.e. the operation in which the phase shift amounts from the correlator 105 are four data described by d1, d2, d3, d4 and expanded to eight data, i.e. the correction amounts for eight ultrasonic transducers.

First, the FFT means 801 carries out the FFT operation for the phase shift amounts d1, d2, d3, d4. Assume that the result thereof, i.e. the calculated values are f1, f2, f3, f4. The result of FFT is expanded to (f1, f2, 0, 0, 0, 0, f3, f4) by filling zeros therein. The IFFT (inverse fast Fourier transform) is carried for (f1, f2, 0, 0. 0, 0, f3, f4). Values equal to double the real part of the calculation result constitute correction amounts Da, Db, Dc, Dd, De Df, Dg, Dh expanded to 8 data from the phase shift amounts d1, d2, d3, d4. The constant multiplied after IFFT, however, is determined from the ratio between the number of data after correction and the number of data before correction according to the definition of FFT.

As described above, with the ultrasonic diagnostic apparatus according to this fourth embodiment, the expanding section 106 is configured with the FFT means 801 and the IFFT means 802 so that the correction amount for each ultrasonic transducer can be accurately determined. Therefore, the distortion of the received wave signal, i.e. the phase shift of the received wave signal attributable to the ununiformity in an human body can be removed accurately. Thus, the distortion of the ultrasonic beam output from the second adding section 104 can be reduced for an improved resolution of the ultrasonic image. As a result, S/N of the ultrasonic image can be further improved.

In the ultrasonic diagnostic apparatus according to the first to fourth embodiments, the delay time set in the delay section 102 is calculated by the expanding section 106, to which the invention is not limited. For example, a configuration can of course be employed in which based on the correction amount calculated by the expanding section 106, the control means included in the delay section 102 adds the correction amount to the initial delay time and thereby sets a delay time in each delay element.

Also, with the ultrasonic diagnostic apparatus according to the first to fourth embodiments, the expanding section 106 is so configured as to calculate the correction amount for the next received data signal based on the immediately preceding data signal received. The invention is not limited to such a configuration, but of course applicable to the received wave data signals preceding to the immediately preceding signal or a combination thereof.

The invention achieved by the present inventor has been described specifically above with reference to embodiments thereof. The present invention, however, is not confined to the aforementioned embodiments but can of course be variously modified without departing from the spirit and scope thereof.

INDUSTRIAL APPLICABILITY

The effects obtained by representative embodiments of the invention disclosed herein are briefly explained below.

(1) The distortion of the received wave signals due to the ununiformity in an human body can be reduced accurately with a small circuit scale.

(2) The resolution of an ultrasonic image can be improved.

(3) The efficiency of diagnosis of a subject can be improved.

What is claim is:

1. An ultrasonic diagnostic apparatus comprising a probe including an arrangement of elements for transmitting and receiving an ultrasonic pulse to and from the interior of a subject, delay means for delaying the wave signal received from each element of said probe, and a plurality of adder means connected in series to the output of said delay means for adding the output signals in the preceding stage and forming an ultrasonic beam, characterized by further comprising correlation means for calculating the correlation of two or more output signals of any of said adder means and delay correcting means for estimating as many delay correction amounts as the input signals to said delay means from the time difference between adjacent signals generated from said correlation means and correcting the delay time of the received signals, and characterized in that the number of input signals to said delay means is a multiple equal to the power of 2 of the input signals to said correlation means.

2. An ultrasonic diagnostic apparatus comprising a probe including an arrangement of elements for transmitting and receiving an ultrasonic pulse to and from the interior of a subject, delay means for delaying the wave signal received from each element of said probe, and a plurality of adder means connected in series to the output of said delay means for adding the output signals in the preceding stage and forming an ultrasonic beam, characterized by further comprising correlation means for calculating the correlation of two or more output signals of any of said adder means and delay correcting means for estimating as many delay correction amounts as the input signals to said delay means from the time difference between adjacent signals generated from said correlation means and correcting the delay time of the received signals, and characterized in that said delay correction means estimates the delay correction amount of elements other than one of the elements arranged on the outermost side based on the delay time of said one of the elements.

3. An ultrasonic diagnostic apparatus characterized by comprising:

a probe including an arrangement of elements for transmitting and receiving ultrasonic pulses to and from the interior of an organism;

delay means for delaying each of the received wave signals of a plurality of the elements of the probe for realizing the desired focus characteristics of each of said received wave signals;

first adder means for producing a plurality of sum signals by adding the received wave signals of the elements through said delay means every the received wave signal groups of a predetermined number of adjacent elements;

second adder means for producing one output signal indicating an ultrasonic echo response by adding said plurality of the sum signals to each other;

correlation means for detecting the phase difference between adjacent ones of the sum signals; and delay correction means for calculating the delay correction amount corresponding to each of said sum signals by sequentially totalizing the phase differences between adjacent sum signals output from said correlation means, calculating the delay correction amount for each received wave signal of a plurality of said elements by interpolation operation from the delay correction amount corresponding to each of said sum signals and correcting the delay of each received wave signal of a plurality of said elements given in said delay means.

4. An ultrasonic diagnostic apparatus as described in claim 3, characterized in that said delay correction means includes correction amount calculation means for calculating a delay correction amount corresponding to each of said received wave signal groups by sequentially totalizing the phase differences between the adjacent signals, Fourier transform means for carrying out the Fourier transformation of the output of said correction amount calculation means, interpolation means for expanding by inserting zero data into the data string in the Fourier space constituting an output of said Fourier transform means, and inverse Fourier transform means for producing a delay correction amount from each of said received wave signal of a plurality of said elements by inverse Fourier transformation of the data string in the expanded Fourier space thereby.

* * * * *